United States Patent [19]

Kok et al.

[11] Patent Number: 5,254,443
[45] Date of Patent: Oct. 19, 1993

[54] PHOTOGRAPHIC DIRECT POSITIVE MATERIAL CONTAINING A MASKED BENZOTRIAZOLE STABILIZER

[75] Inventors: Piet Kok, Gent; Jean-Marie O. Dewanckele, Drongen, both of Belgium

[73] Assignee: Agfa-Gevaert, N.V., Mortsel, Belgium

[21] Appl. No.: 915,673

[22] Filed: Jul. 21, 1992

[30] Foreign Application Priority Data

Aug. 13, 1991 [EP] European Pat. Off. ........... 91202073
Dec. 16, 1991 [EP] European Pat. Off. ........... 91203295

[51] Int. Cl.$^5$ .......................... G03C 5/29; G03C 1/34
[52] U.S. Cl. .................................. 430/401; 430/487; 430/567; 430/598; 430/600; 430/614
[58] Field of Search ............... 430/567, 598, 600, 614, 430/401, 487

[56] References Cited

U.S. PATENT DOCUMENTS

4,572,892 2/1986 Hoyen ........................... 430/598

FOREIGN PATENT DOCUMENTS

765944 10/1971 Belgium ........................ 430/614

Primary Examiner—Janet C. Baxter
Attorney, Agent, or Firm—Breiner & Breiner

[57] ABSTRACT

A photographic direct positive material is disclosed comprising a support and one or more radiation sensitive emulsion layers containing internal latent image-forming silver halide grains characterized in that at least one of said emulsion layers further contains a masked stabilizer corresponding to general formula (I):

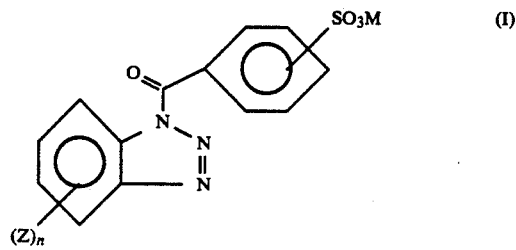

wherein Z represents a lower alkyl group, a nitro group or a halogen atom, n=0 to 4, and M represents a positive counterion.

Preferred compounds are 1-(2-sulphonatobenzoyl)-5-methyl-benzotriazole, 1-(2-sulphonatobenzoyl)-6-methyl-benzotriazole or a mixture of both.

The masked stabilizer is preferably incorporated in the emulsion layer(s). The material preferably further contains a nucleating agent. Improved direct positive sensitometric properties and wider exposure latitude before encountering rereversal are obtained.

12 Claims, No Drawings

PHOTOGRAPHIC DIRECT POSITIVE MATERIAL CONTAINING A MASKED BENZOTRIAZOLE STABILIZER

DESCRIPTION

1. Field of the Invention

The present invention relates to direct positive black-and-white photographic materials. More particularly it relates to direct positive materials containing masked stabilizers of a particular type.

2. Background of the Invention

Photographic black-and white materials producing a density upon development which is directly related to the radiation received on exposure are termed negative working. From such a negative image a positive image resembling the original recorded scene can be produced by copying it on another negative working material. Direct positive images are understood in photography to be formed without intervention of a negative image by development of photographic emulsion layers containing specially designed so-called direct positive emulsions.

In this method of photographic imaging the application of two main types of emulsions can be distinguished, the first one being externally fogged emulsions, usually containing an electron acceptor, the second one being unfogged internal latent image-forming emulsions, which are positive-working by fogging development, preferably in the presence of a so-called nucleating agent.

Surface-fogged emulsions are disclosed e.g. in Kendall U.S. Pat. No. 2,541,472, Schouwenaars GB 723,019, Illingsworth U.S. Pat. No. 3,501,307, Berriman U.S. Pat. No. 3,367,778 and *Research Disclosure*, Vol 134, Jun. 1975, Item 13452.

Internal latent image-forming silver halide grains are disclosed in e.g. Ives U.S. Pat. No. 2,563,785, Evans U.S. Pat. No. 3,761,276, Knott U.S. Pat. No.2,456,953 and Jouy U.S. Pat. No. 3,511,662. Further patents include Davey U.S. Pat. No. 2,592,250, which describes internal sensitive emulsions prepared by conversion, Porter U.S. Pat. No. 3.206,313, which discloses direct positive emulsions of a particular core-shell type, Milton U.S. Pat. No. 3,761,266, illustrating chloride rich direct positive emulsions, Gilman U.S. Pat. No. 3,761,267, Atwell U.S. Pat. No. 4,035,185, and Daubendiek U.S. Pat. No. 4,504,570, which discloses direct positive emulsions of the internal latent image-forming type containing tabular grains.

In conventional silver halide photography, both negative or direct positive working, so-called stabilizers or anti-foggants are well known ingredients which can be incorporated in photographic materials and/or in photographic developing solutions. Their principal function consists in minimizing the obtained fog level on developing exposed photographic materials and/or to reduce the rise of development fog after prolonged storage of the photographic material compared to the fog level of a freshly coated material. Numerous chemical classes of stabilizers are disclosed in photographic scientific and patent literature. Suitable examples are e.g. the heterocyclic nitrogen-containing compounds such as benzothiazolium salts, imidazoles, nitroimidazoles, benzimidazoles, nitrobenzimidazoles, chlorobenzimidazoles, bromobenzimidazoles, indazoles, nitroindazoles, mercaptothiazoles, mercaptobenzothiazoles, mercaptobenzimidazoles, mercaptothiadiazoles, aminotriazoles, benzotriazoles (preferably 5-methyl-benzotriazole), nitrobenzotriazoles, mercaptotetrazoles, in particular, 1-phenyl -5-mercapto-tetrazole, mercaptopyrimidines, mercaptotriazines, benzothiazoline-2-thione, oxazoline-thione, triazaindenes, tetrazaindenes and pentazaindenes, especially those described by Birr in Z. Wiss. Phot. 47 (1952), pages 2-58, triazolopyrimidines such as those described in GB 1,203,757, GB 1,209,146, JA-Appl. 75-39537, and GB 1,500,278, and 7-hydroxy-s-triazolo-[1,5-a]-pyrimidines as described in U.S. Pat. No. 4,727,017, and other compounds such as benzenethiosulphonic acid, toluenethiosulphonic acid, benzenethiosulphinic acid and benzenethiosulphonic acid amide. A review of useful compounds is published in Research Disclosure No 17643 (1978). Chapter VI.

As is well known in the art direct positive silver halide emulsions exhibit various disadvantages as compared to negative working emulsions. The high level of sensitivity which can be routinely attained with negative emulsions cannot easily be reached with direct positive emulsions. It is not easy to reconciliate the various demands of high maximum density, good contrast, low minimum density and sufficient speed. More particularly direct positive emulsions of the internal sensitivity type can suffer from a second disadvantage known as rereversal on overexposure. This means that, with increasing overexposure starting from an exposure level beyond the toe of the direct positive sensitometric curve, a negative gradient starts to build up. As a practical result the high-lights of an original scene which contains a broad range of reflected light intensities tend to be reproduced as highly disturbing negative images.

Several patent publications disclose particularly usefull classes of antifoggants or stabilizers in connection with direct positive materials in order to counteract their specific disadvantages. So Unexamined Japanese Patent Publication (Kokai ) 62-229134 describes benzotriazoles in backing layers of materials containing core-shell type direct positive emulsions in order to improve processing stability. The addition of several kinds of mercapto-substituted N-containing heterocyclic compounds to direct positive emulsions of the internal sensitivity type are disclosed in Unexamined Japanese Patent Publications (Kokai) 63-029752, 01-197742, 63-040148 and 63-040148. In Kokai 57-096331 the addition after physical maturation to direct positive emulsions of specific mercaptotriazoles in order to improve raw stock stability is described.

Stauffer U.S. Pat. No. 2,497,917 recognized that certain antifoggants when used in internal latent image-forming direct positive elements not only reduce the minimum density but also increase maximum density. Members of this special class of antifoggants are known to be effective whether incorporated in the photographic element itself or in a developing solution. Further applications of maximum density enhancing antifoggants are illustrated in Evans U.S. Pat. No. 3.761,276 cited above. Hoyen U.S. Pat. No. 4,572,892 discloses a black-and-white direct positive photographic element comprising one or more emulsion layers containing internal latent image-forming silver halide grains and further a maximum density enhancing 1,2,3-triazole antifoggant (preferably a benzotriazole derivative) which has to be incorporated in an undercoat layer between the emulsion layer(s): in the preferred embodiment a nucleating agent is present, e.g. an arylhydrazide derivative. An improved direct positive sensitometry is claimed together with an extended overexposure margin before rereversal occurs. However the practice of this procedure exhibits the technological and economical disadvantage of the requirement for an extra undercoat layer. Further the solubility in water of benzotriazole derivatives is rather limited so that for the incorporation of higher amounts the use of organic solvents which are ecologically disadventageous are needed.

The present invention relates to a further improvement to the teachings of U.S. Pat. No. 4,572,892.

It is an object of the present invention to provide a photographic direct positive material, working by means of internal image-forming silver halide emulsion grains, with excellent sensitometric characteristics, being high maximum density, low minimum density, good contrast and sensitivity.

It is a further object of the present invention to provide a direct positive material with sufficient overexposure latitude before encountering rereversal.

It is still a further object of the present invention to realize the benefits of such direct positive material without requirement for an intermediate layer between support and emulsion layer(s), also called undercoat layer.

3. Summary of the Invention

The objects of the present invention are realized by providing a photographic direct positive material comprising a support and one or more radiation sensitive emulsion layers containing internal latent image forming silver halide grains characterized in that at least one of said emulsion layers further contains a compound corresponding to general formula (I):

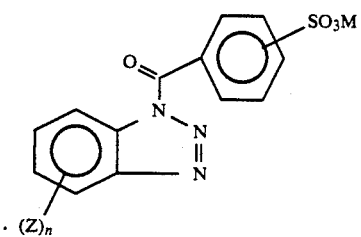

wherein Z represents a lower alkyl group, a nitro group or a halogen atom, n=0 to 4, and M represents a positive counterion.

According to a further aspect of this invention the described direct positive material is meant to be processed in a surface developer (a) in the presence of a nucleating agent or (b) with light flashing of the photographic element. However procedure (a) constitutes the preferred embodiment. Most preferably an arylhydrazide nucleating agent is used which is preferably incorporated in an emulsion layer too.

4. DETAILED DESCRIPTION OF THE INVENTION

The 1-(2-sulphonatobenzoyl)-benzotriazole derivatives represented by formula (I) and used in accordance with the present invention form a subclass of a class of so-called masked stabilizers which was disclosed for the first time in European Patent Application, filed 13.08.91 under applic. No. 91202073.2. The term "masked stabilizer" refers to the fact that these compounds are easily decomposed (or "demasked") to form the free stabilizer molecule under the alkaline pH conditions commonly occuring during the development step.

Thus, pages 12 and 13 of the European Patent Application Ser. No. 91202073.2 filed Aug. 13, 1991 disclose the following:

1.a. Preparation of
1-(2-sulphonatobenzoyl)-5-nitroindazole
trimethylamine salt

To a suspension of 179.5 g (1.1 mole) of 5-nitroindazole and 184 g (1 mole) of o-sulphobenzoic acid anhydride in 2000 ml of dry acetone were added dropwise while stirring 153 ml (1.1 mole) of triethylamine at reflux temperature. Then the suspension was refluxed for another 6 hours. The precipitate was filtered off at room temperature, washed with acetone and dried. Yield: 323 g (72%); melting point: 210° C.; chemical structure confirmed by NMR analysis.

1.b. Preparation of
1-(2-sulphonatobenzoyl)-5-nitroindazole potassium salt

To a suspension of 268.8 g (0.6 mole) of 1-(2-sulphonatobenzoyl)-5-nitroindazole trimethylamine salt in 540 ml of methanol and 360 ml of water was added at room temperature while stirring a saturated potassium chloride solution containing 134 g (1.8 mole) of potassium chloride in 400 ml of water. Then the suspension was stirred for another two hours. After waiting for 12 hours the precipitate was filtered off, washed with 480 ml of a water/methanol (1/1) mixture and finally dried. Yield: 217 g (94%); melting point > 300° C.

1.c. Preparation of
1-(2-sulphonatobenzoyl)-benzotriazole triethylamine salt

This compound was prepared in a similar way as explained in example 1.a. with the exception that 1.1 mole of benzotriazole was used instead of 5-nitroindazole. Yield: 56%; melting point 180° C.

1.d. Preparation of
1-(2-sulphonatobenzoyl)-5-methylbenzotriazole triethylamine salt This compound was prepared in a similar way as explained in example 1.a. with the exception that 1.1 mole of 5-methyl-benzotriazole was used instead of 5-nitroindazole. A mixture of the two positional isomers was obtained. Yield: 46%; melting point: about 167° C.

Examples of useful masked stabilizers (MS) according to formula (I) are set forth in Table 1:

TABLE 1

| | |
|---|---|
| MS-1 | 1-(2-sulphonatobenzoyl)-benzotriazole |
| MS-2 | 1-(2-sulphonatobenzoyl)-5-methylbenzotriazole |
| MS-3 | 1-(2-sulphonatobenzoyl)-6-methylbenzotriazole |
| MS-4 | 1-(2-sulphonatobenzoyl)-5-ethylbenzotriazole |
| MS-5 | 1-(2-sulphonatobenzoyl)-5-bromobenzotriazole |
| MS-6 | 1-(2-sulphonatobenzoyl)-5-chlorobenzotriazole |
| MS-7 | 1-(2-sulphonatobenzoyl)-4-nitro-6-chlorobenzotriazole |
| MS-8 | 1-(2-sulphonatobenzoyl)-5,6-dichlorobenzotriazole |

The best results are obtained with compound MS-2 and with compound MS3, as will become clear from the examples later on. During the acylation reaction starting from free 5-methylbenzotriazole a mixture of the two positional isomers 1-(2-sulphonatobenzoyl)-5-methylbenzotriazole (MS-2) and 1-(2-sulphonatobenzoyl)-6-methylbenzotriazole (MS-3) are formed. On demasking they both form the same methylbenzotriazole again. So the isomers MS-2 and MS-3 can be used as a mixture.

It is specifically contemplated that in the practice of this invention the masked stabilizer can be incorporated in the emulsion layer (or one of the emulsion layers) itself and that there is no need for an extra undercoat layer as opposed to the teaching of U.S. Pat. No. 4,572,892, cited above. We think this is due to the special masked character of the compounds used in accordance with the present invention. If one would incorporate, contrary to the teachings of U.S. Pat. NO. 4,572,892, a free benzotriazole stabilizer into the emulsion layer(s), this compound would be prematurely adsorbed to the silver halide grain surface; as a consequence the nucleation phase would be hampered and the development rate slowed down resulting in a low direct positive maximum density. This problem can be overcome, according to U.S. Pat. No. 4,572,892, by applying the free stabilizer in an extra undercoat, from which it takes some time to diffuse to the emulsion layer, or alternatively by incorporating the stabilizer in a masked form in the emulsion layer as proposed in this invention.

Thanks to their higher solubily as compared to the corresponding free stabilizers the masked benzotriazoles can simply be added as aqueous solutions to the coating solution. The concentration of the masked benzotriazoles in the emulsion layer is preferably comprised between $10^{-4}$ and $5 \times 10^{-2}$ mole per mole of silver halide.

Preferred latent image-forming silver halide emulsions are so-called core-shell emulsions consisting of a core and at least one shell with the same or different halide compositions. Both shell and core can mutually independently be composed of silver bromide, silver chloride, silver chlorobromide, silver chloroiodide, silver bromoiodide and silver chlorobromoiodide. The emulsions can show a coarse, medium or fine average grain size and be bounded by (100), (111), (110) crystal planes or combinations thereof. Also high aspect ratio tabular core-shell emulsion grains can be contemplated as disclosed in U.S. Pat. No. 4,504,570. The core-shell emulsions contain internal sensitization sites which can be of various nature and which form an internal latent image upon exposure.

A first type of core-shell emulsions contains internal physical sensitization sites formed by crystallographic irregularities in the phase bounderies between a core and a shell of distinctly different halide composition, e.g. a silver bromide core and a silver bromoiodide shell with a relative high iodide percentage.

Another simple method for applying internal sensitization sites consists of incorporating a polyvalent metal ion dopant in the core grains during their formation. This metal dopant can be placed in the reaction vessel prior to precipitation or it can be added to one or more of the solutions taking part in the precipitation. Preferred polyvalent metal dopants are elements of group VIII of the Periodic System, e.g. Iridium, as disclosed in U.S. Pat. No. 3,367,778, or Rhodium. They are preferably used in the form of a soluble salt or coordination complex. The usual concentration range is comprised between $10^{-8}$ and $10^{-4}$ mole per mole of silver halide.

The most common method of creating internal sensitization sites consists of interrupting the precipitation after completion of the core and apply chemical sensitization or even fogging to this core, after which process the precipitation of the shell is resumed. The usual chemical ripening agents containing middle-chalcogen elements like sulphur, selenium and tellurium can be used as was disclosed e.g. in U.S. Pat. No. 3,761,276. Preferably they are combined with compounds containing noble metal atoms, e.g. gold. Contrast can be controlled by optimizing the ratio of middle-chalcogen amount to gold sensitizer amount as is described in U.S. Pat. No. 4,035,185.

The choice of the halide composition of the shell portion will depend on the requirements of the specific photographic application. In order to achieve fast developability emulsion shells with a high chloride content are best suited. On the contrary when high sensitivity is most important bromide or iodobromide grain shells are to be preferred. The shell portion of the grain must contain a sufficient percentage of the total silver halide in order to restrict access of a surface developer to the internal sensitization centers. The surface of the finished core-shell emulsion grains can be chemically sensitized or not. For obtaining good reveral speed and maximum density a moderate degree of surface sensitization using conventional techniques can be applied. This degree of chemical sensitization is limited to that which will realize an optimal balance between internal and surface sensitivity, the internal sensitization usually remaining predominant.

It is specifically contemplated that in order to control sensitometric characteristics two or more internal latent image-forming emulsions can be blended before coating and thus be applied in the same emulsion layer. Alternatively several different emulsions can be used each in a different emulsion layer arranged in a pack. However in a most preferred embodiment of the present invention simply one emulsion layer is coated containing one direct positive emulsion or a blend of several direct positive emulsions.

The internal latent image-forming emulsions can, if desired, be spectrally sensitized according to the exposure source to be used depending on the specific photographic application. Dyes that can be used for the purpose of spectral sensitization include cyanine dyes, merocyanine dyes, complex cyanine dyes, complex merocyanine dyes, hemicyanine dyes, styryl dyes and hemioxonol dyes. Particularly valuable dyes are those belonging to the cyanine dyes, merocyanine dyes and complex merocyanine dyes as described by F. M. Hamer in "The Cyanine Dyes and Related Compounds", 1964, John Wiley & Sons. The process of spectral sensitization can take place at any stage of the emulsion preparation but most commonly spectral sensitization is undertaken subsequent to the completion of surface chemical sensitization, if any.

A preferred orthochromatic spectral sensitizing dye (SD-1) is represented by following chemical formula:

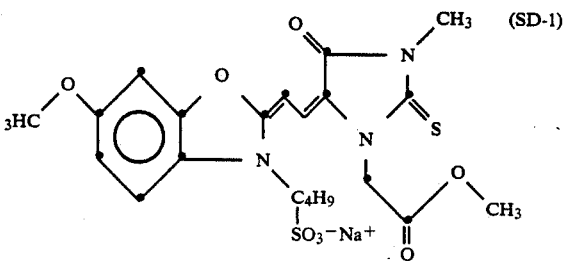

In order to promote the formation of a direct positive image the photographic materials of the present invention can be image-wise exposed and then subjected to uniform flash lighting during processing. Preferably however the direct positive image is formed with the aid of a so-called nucleating agent (or development nucleator) which triggers development. This nucleating agent can be present in the developing solution but most preferably it is present in the photographic material itself. Since in the preferred embodiment of this invention there is no undercoat non-light sensitive layer the nucleating agent is preferably incorporated in the emulsion layer(s). When used in the silver halide emulsion layer(s) the development nucleators are present in a concentration of preferably $10^{-5}$ mole to $10^{-1}$ mol per mole of silver halide.

A first class of suitable development nucleators for use in accordance with the present invention are the hydrazide-type compounds corresponding to the following general formula N-1:

$$R^1-NH-NH-CO-R^2 \quad \text{(N-1)}$$

wherein each of $R^1$ and $R^2$ independently represent hydrogen, an alkyl group, a substituted alkyl group, an aryl group, or a substituted aryl group.

Preferred development nucleators for use in accordance with the present invention are aryl hydrazides e.g. 1-formyl-2-phenyl-hydrazide, 1-p-acetamidophenyl-2-acetyl-hydrazide, and 1-[2-(2,4-di-tert-pentyl-phenoxy)-propionamidophenyl]-2-formyl-hydrazide.

Another class of suitable hydrazide-type development nucleators are hydrazides comprising a heterocyclic nitrogen-containing nucleus or a substituted heterocyclic nitrogen-containing nucleus e.g. a thiohydantoin nucleus and a mercaptotetrazolyl nucleus. Examples of such compounds are the following compounds N-2 and N-3:

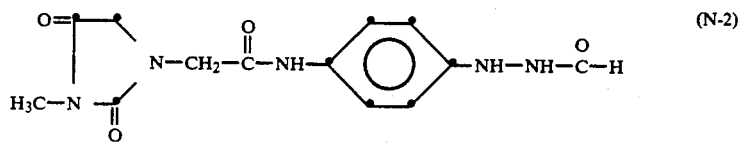

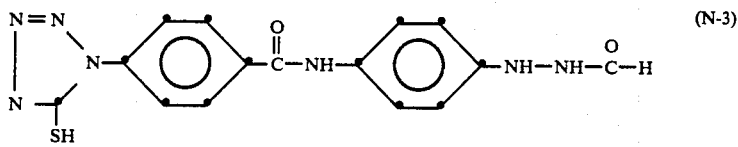

A preferred class of hydrazide-type development nucleators for use in accordance with the present invention, which comprise a heterocyclic nitrogen-containing nucleus are the hydrazines carrying a pyrazolidin-3-one-1-yl-phenyl group or a substituted pyrazolidin-3-one-1-yl-phenyl group. Examples of such preferred development nucleators are the compounds according to the following structural formulae N-4 and N-5:

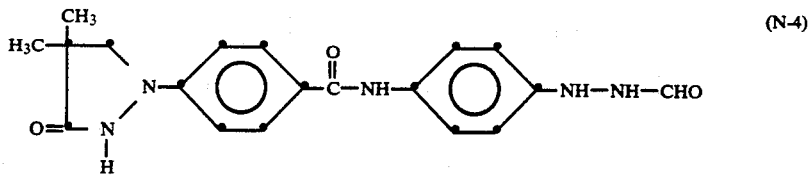

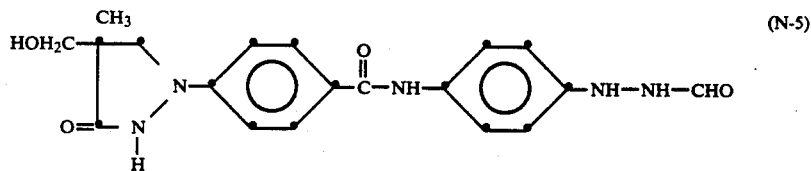

An interesting class of development nucleators corresponding to general formula N-1 are the aryl hydrazides containing water-solubilizing polyhydroxy moieties. Representatives of this class correspond to the following general formula N-6:

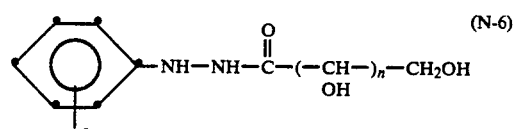

wherein
n is a positive integer ranging from 1 to 10 and
$R^3$ is hydrogen, an alkyl group, a substituted alkyl group, an aryl group, a substituted aryl group, a heterocyclic group, or a substituted heterocyclic group.

A suitable example of a heterocyclic group represented by $R^3$ in general formula N-6 is a pyrazolidin-3-one-1-yl group, which may be substituted.

Examples of development nucleators corresponding to general formula N-6 are the compounds, in which n is 4 or 5 and $R^3$ stands for hydrogen.

Another preferred class of aromatic hydrazide nucleating agents are those in which the aromatic nucleus is substituted with one or more groups to restrict mobility and, preferably promote adsorption of the hydrazide derivative to the silver halide grain surface. Preferred hydrazides of this kind are represented by following general formula (N-7)

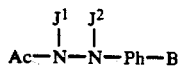  (N-7)

wherein
Ac is an acyl group,
$J^1$ is hydrogen and $J^2$ is a sulphinic acid radical or vice versa,
Ph is a phenylene or substituted phenylene group, and
B is a moiety capable of restricting mobility, such as a ballasting or an adsorption promoting moiety.

Hydrazides of this type are disclosed by Hess U.S. Pat. No. 4,478,928. A preferred type of sulphinic acid radical is represented by the following:

wherein Ar is an aryl group or substituted aryl group, preferably phenyl or naphthyl. A still further preferred class of aromatic hydrazide nucleating agents are acyl-hydrazinophenylthioureas as disclosed by Leone U.S. Pat. No. 4,030,925 and U.S. Pat. No. 4,276,364. other variants are described by von Konig U.S. Pat. No. 4,139,387 and Adachi GB 2,012,443.

Still another preferred class of nucleating agents of the hydrazide type consists of N-(acylhydrazino-phenyl)thioamide compounds as disclosed in Leone U.S. Pat. No. 4,080,207. Further preferred compounds are triazolo-substituted phenyl hydrazide nucleating agents as described by Sidhu U.S. Pat. No. 4,278,748. Comparable nucleating agents having a somewhat broader range of adsorption promoting groups are disclosed in GB 2,011,391.

Other useful hydrazine and hydrazide nucleating agents have been disclosed in e.g. Research Disclosure Item 23510 Vol. 235, Nov. 10, 1983 and in U.S. Pat. No. 4,269,929, US 4,243,739, U.S. Pat. No. 4,272,614. Recently new hydrazine and hydrazide derivatives or new combinations with other useful ingredients have been disclosed in e.g. EP 0 254 195, U.S. Pat. No. 4,915,354, DE 3 629 078, EP 0 311 009, U.S. Pat. No. 4,816,373, U.S. Pat. No. 4,686,167, EP 0 351 077, U.S. Pat. No. 4,833,064, U.S. Pat. No. 4,937,160, U.S. Pat. No. 4.912,016, U.S. Pat. No. 4,950,578, U.S. Pat. No. 4,975,354, U.S. Pat. No. 4,988,604. EP 0 399 460, U.S. Pat. No. 4,971,890, U.S. Pat. No. 4,994,365, EP 0 420 005, EP 0 398 355, U.S. Pat. No. 4,971,888, U.S. Pat. No. 4,960,672, EP 0 393 711, EP 0 393 720, EP 0 393 721, and Japanese Unexamined Patent Publications 63-306438, 63-234245, 63-234244, 01-105941, 01-179982, 01-201650, 01-235943, 01-296238, 01-090439, 01-055549. These hydrazine and hydrazide compounds can likewise be used in the present invention.

A second general class of suitable development nucleators consists of reactive N-substituted cycloammonium quaternary salts corresponding to the following general formula N-8:

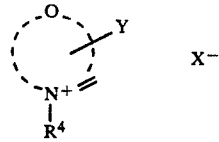  (N-8)

wherein Q represents the necessary atoms to close an heterocyclic 5- or 6-membered ring or ring system, and $R^4$ and Y can represent several kinds of substituents depending on the specific chemical class. Useful classes of N-substituted cycloammonium derivatives are disclosed in e.g. U.S. Pat. No. 3,615,615, U.S. Pat. No. 3,759,901, U.S. Pat. No. 3,734,738, U.S. Pat. No. 3,719,494, U.S. Pat. No. 4,115,122, U.S. Pat. No. 4,471,044 and Research Disclosure, Vol. 232, August 1983, Item 23213. Recent disclosures on N-substituted cycloammonium derivatives include e.g. Japanese Unexamined Patent Publications 01-61638, 01-217338, 01-217339, 01-20024 and 01-179142.

Other classes of suitable development nucleators are e.g.: sulphur compounds e.g. thiourea dioxide, phosphonium salts e.g. tetra(hydroxymethyl)phosphonium chloride, hydroxylamine, bis-(p-aminoethyl)-sulphide and water-soluble salts thereof, reductic acid and derivatives thereof e.g. 4,4,5,5-tetramethyl-reductic acid, kojic acid, ascorbic acid, 2-hydroxy-1,3-cyclohexanedione, 2-acetoxy1,2-di(2-pyridyl)-ethanone, 2-hydroxy-1,2-di(2-pyridyl)-ethanone.

Mixtures of at least two of the above-mentioned development nucleators can be used advantageously.

Prior to the coating of the composition that will form the photographic layer comprising at least one development nucleator, the development nucleator(s) can be dissolved in an organic solvent, e.g. N-methyl-pyrrolidone, and added to said composition.

Alternatively the development nucleator(s) can be added in dispersed form to the hydrophilic colloid composition that will form said emulsion layer. In this case this dispersion can be prepared by dissolving these nucleators first in at least one water-immiscible, oil-type solvent or oil-former, adding the resulting solution to an aqueous phase containing a hydrophilic colloid preferably gelatin and a dispersing agent, passing the mixture through a homogenizing apparatus so that a dispersion of the oily solution in an aqueous medium is formed, mixing the dispersion with a hydrophilic colloid composition e.g. a gelatin silver halide emulsion, and coating the resulting composition in the usual manner to produce a system in which particles of development nucleator(s), surrounded by an oily membrane, are distributed throughout the gel matrix. The dissolution of the development nucleator(s) in the oil-former may be facilitated by the use of an auxiliary low-boiling water-immiscible solvent. e.g. ethylacetate, which is removed afterwards by evaporation.

The binder of the photographic element, especially when the binder used is gelatin, can be hardened with appropriate hardening agents such as those of the epoxide type, those of the ethylenimine type, those of the vinylsulfone type e.g. 1,3-vinylsulphonyl-2-propanol, chromium salts e.g. chromium acetate and chromium alum, aldehydes e.g. formaldehyde, glyoxal, and glutaraldehyde, N-methylol compounds e.g. dimethylolurea and methyloldimethylhydantoin, dioxan derivatives e.g. 2,3-dihydroxy-dioxan, active vinyl compounds e.g. 1,3,5-triacryloyl-hexahydro-s-triazine, active halogen compounds e.g. 2,4-dichloro-6-hydroxy-s-triazine, and mucohalogenic acids e.g. mucochloric acid and mucophenoxychloric acid. These hardeners can be used alone or in combination. The binders can also be hardened with fast-reacting hardeners such as carbamoylpyridinium salts as disclosed in U.S. Pat. No. 4,063,952.

The photographic element of the present invention may further comprise various kinds of surface-active agents in the photographic emulsion layer or in at least one other hydrophilic colloid layer. Suitable surface-active agents include non-ionic agents such as saponins, alkylnne oxides e.g. polyethylene glycol, polyethylene glycol/polypropylene clycol condensation products, polyethylene glycol alkyl ethers or polyethylene glycol alkylaryl ethers, polyethylene glycol esters, polyethylene glycol sorbitan esters, polyalkylene glycol alkylamines or alkylamides, silicone-polyethylene oxide adducts, glycidol derivatives, fatty acid esters of polyhydric alcohols and alkyl esters of saccharides; anionic agents comprising an acid group such as a carboxy, sulpho, phospho, sulphuric or phosphoric ester group; ampholytic agents such as aminoacids, aminoalkyl sulphonic acids, aminoalkyl sulphates or phosphates, alkyl betaines, and amine-N-oxides; and cationic agents such as alkylamine salts, aliphatic, aromatic, or heterocyclic quaternary ammonium salts, aliphatic or heterocyclic ring-containing phosphonium or sulphonium salts. Such surface-active agents can be used for various purposes e.g. as coating aids, as compounds preventing electric charges, as compounds improving slidability, as compounds facilitating dispersive emulsification, as compounds preventing or reducing adhesion. Preferred surface-active agents are compounds containing perfluorinated alkyl groups.

The photographic element of the present invention may further comprise various other additives such as e.g. compounds improving the dimensional stability of the photographic element, antistatic agents, spacing agents, light absorbing dyes. e.g. antihalation dyes, filter dyes or acutance dyes, lubricants, opacifying compounds, e.g. titanium dioxide, and plasticizers.

Antistatic agents can be used in one or more of the layers on the emulsion side or in a backing layer.

Suitable additives for improving the dimensional stability of the photographic element are e.g. dispersions of a water-insoluble or hardly soluble synthetic polymer e.g. polymers of alkyl(meth)acrylates, alkoxy(meth)acrylates, glycidyl (meth)acrylates, (meth)acrylamides, vinyl esters, acrylonitriles, olefins, and styrenes, or copolymers of the above with acrylic acids, methacrylic acids, Alpha-Beta-unsaturated dicarboxylic acids, hydroxyalkyl (meth)acrylates, sulphoalkyl (meth)acrylates, and styrene sulphonic acids.

Spacing agents can be present of which, in general, the average particle size is comprised between 0.2 and 10 micron. Suitable spacing agents can be made e.g. of polymethyl methacrylate, of copolymers of acrylic acid and methyl methacrylate, and of hydroxypropylmethyl cellulose hexahydrophthalate. Other suitable spacing agents have been described in U.S. Pat. No. 4,614,708. Spacing agents can also serve as matting agents. Other common matting agents consist of silica particles of which different size classes can be used.

In the direct positive material of the present invention non-light sensitive hydrophilic colloid layers can be present, e.g. a protective layer and one or more backing layers. As stated above no undercoat layer is needed since the masked stabilizers are incorporated in the emulsion layers.

The support of the photographic material may be opaque or transparent, e.g. a paper support or resin support. When a paper support is used preference is given to one coated at one or both sides with an Alpha-olefin polymer, e.g. a polyethylene layer which optionally contains an anti-halation dye or pigment. It is also possible to use an organic resin support e.g. cellulose nitrate film, cellulose acetate film, polyvinyl acetal film, polystyrene film, polyethylene terephthalate film, polycarbonate film, polyvinylchloride film or poly-Alpha-olefin films such as polyethylene or polypropylene film. The thickness of such organic resin film is preferably comprised between 0.07 and 0.35 mm. These organic resin supports are preferably coated with a subbing layer which can contain water insoluble particles such as silica or titanium dioxide.

The photographic direct positive materials of the present invention can be exposed in any convenient way according to their particular application, e.g. by daylight or by artificial light like tungsten light, xenon, metal-halogen lamps, quartz-halogen lamps, by laser sources or invisible radiation like ultraviolet, X-rays and infrared.

The processing of the photographic materials of the present invention proceeds in a surface developer composed according to specifications dependent on the particular use of the material.

The developing solution preferably contains one or more developing agents, sulphite ions, bromide ions and polyalkyleneoxides. Preferred developing agents are e.g. hydroquinone and derivatives. 3-pyrazolidinone derivatives like 1-phenyl-5-pyrazolidinone ("Phenidone") and analogues, aminophenols, hydroxylamin, hydrazine derivatives, and ascorbic acid and analogues. Other adjuvants well known to those skilled in the art may be added to the developer liquid of the present invention. A survey of conventional developer addenda is given by Grant Haist in "Modern Photographic Processing"—John Wiley and Sons—New York (1979) 220–224. Examples of such addenda include complexing agents for calcium and magnesium ions, present in hard water, e.g. ethylene diamine tetraacetic acid and analogues compounds. Further can be present anti-foaming agents, surface-active agents, biocedes, thickening agents like polystyrene sulphonate and antioxidants like benzoate and cyclodextrine. The developing liquid can contain so-called anti-sludge agents in order to reduce dirt streaks on developed photographic material. The alkaline pH value of the developing solution is preferably established by means of conventional buffering agents like phosphate buffers, carbonate buffers and borax buffers. The pH can be additionally adjusted to the desired value by means of an alkali hydroxide, e.g. sodium or potassium hydroxide. Finally the solution can contain hardening agents including latent hardeners.

For processing preferably an automatically operating apparatus is used provided with a system for automatic replenishment of the processing solutions.

The development step can be followed by a washing step, a fixing solution and another washing or stabilization step. Finally the photographic material is dried.

The photographic direct positive materials of the present invention can be used in various types of photographic elements such as e.g. in photographic elements for graphic arts, for general amateur and professional photography, for cinematographic recording and duplicating, for radiographic recording and duplicating purposes, and in diffusion transfer reversal photographic elements. A preferred application however is micrographic recording, e.g. in a microfilm for computer output.

The following examples illustrate the invention without however limiting it thereto.

EXAMPLES

Example 1

An octahedral silver bromide core-shell emulsion showing a final average grain size of 0.3 micron was prepared by simultaneous addition of equimolar solutions of silver nitrate and potassium bromide to a stirred aqueous gelatin solution. The precipitation of the core was carried out at 70° C. starting at a pAg of 6.80. After addition of 15% of the total silver the pAg was changed to 8.71 and the precipitation was continued until 50% of the total silver was consumed and an average core diameter of 0.23 micron was reached. After bringing the gelatin/silver ratio to 0.5 by dissolving 1 5 extra gelatin, this core was chemically sensitized by means op $25.8 \times 10^{-3}$ mmole of sodium thiosulphate, $16.3 \times 10^{-3}$ mmole of chloroauric acid and $27.5 \times 10^{-3}$ mmole of p-toluenethiosulphonic acid sodium salt, all expressed per mole of silver halide. A shell was precipitated on this core at a temperature of 50° C. and a pAg of 9.4 7. After completion of the precipitation the gelatin/silver ratio was again adjusted to 0.5 and the core-shell emulsion was chemically ripened using $13.8 \times 10^{-3}$ mmole of sodium thiosulphate, $2.48 \times 10^{-3}$ mmole of aurochloric acid and $26.8 \times 10^{-3}$ mmole of ammonium thiocyanate, all expressed per mole of silver halide.

The finished emulsion was divided in aliquot samples and to each sample were added 1.65 mmole/mole of AgNO$_3$ of spectral sensitizing dye SD-1, 6.6 mmole/mole of AgNO$_3$ of nucleating agent phenylformylhydrazide. Finally various amounts of free benzotriazole (S-1), masked benzotriazole (MS-1), free 5-methylbenzotriazole (S-2) and masked methylbenzotriazole (a mixture of MS-2 and MS-3) were added as indicated in Table 2. Each emulsion sample was coated on a transparent support at a coverage of 4.0 Ag/m$^2$ expressed as AgNO$_3$. Then the coatings were exposed through a continuous wedge on a EG&G sensitometer using a $10^{-5}$ s flashlight and developed at 35° C. in a developer of following composition:

| | |
|---|---|
| N-methyl-p-aminophenol | 15 g |
| sodium sulphite anh. | 110 g |
| sodium hydroxide | 19 g |
| sodium carbonate | 40 g |
| sodium bromide | 3 g |
| hydroquinone | 40 g |
| 2-methylaminoethanol | 40 ml |
| water to make | 1 l |

After development the coatings were treated in a conventional fixing bath and finally washed and dried. The direct positive sensitometric characteristics were evaluated and represented in Table 2a.

A second set of the same coatings was subjected to a treatment of 3 days at 57° C.—34% relative humidity in order to simulate aging properties. Then this second set was exposed, processed and evaluated as the previous series. The results are represented in Table 2b.

TABLE 2A

| coating No | Stabi. | Conc.[1] | Dev · t · (s) | Sensitometry | | | |
|---|---|---|---|---|---|---|---|
| | | | | Dmin | S[2] | Dmax | Delta RR[3] |
| 1 | S-1 | $10^{-3}$ | 30 | 0.10 | 1.60 | 2.2 | 1.10 |
| 2 | MS-1 | $10^{-3}$ | 45 | 0.18 | 1.80 | 3.0 | >1.2* |
| 3 | MS-1 | $10^{-2}$ | 45 | 0.11 | 1.55 | 2.8 | >1.45* |
| 4 | S-2 | $10^{-3}$ | 30 | 0.09 | 1.50 | 2.4 | 1.05 |
| 5 | S-2 | $10^{-2}$ | 60 | 0.08 | 1.35 | 2.6 | 1.20 |
| 6 | MS-2/3 | $10^{-3}$ | 30 | 0.08 | 1.65 | 2.3 | 1.20 |
| 7 | MS-2/3 | $10^{-2}$ | 45 | 0.06 | 1.35 | 2.4 | >1.65* |

TABLE 2b

| coating No | Stabi. | Conc.[1] | Dev · t · (s) | Sensitometry 3 d 57°/34% RH | | | |
|---|---|---|---|---|---|---|---|
| | | | | Dmin | S[2] | Dmax | Delta RR[3] |
| 1 | S-1 | $10^{-3}$ | 30 | 0.21 | 1.75 | 2.4 | 0.50 |
| 2 | MS-1 | $10^{-3}$ | 45 | 0.37 | 1.70 | 3.2 | 0.85 |
| 3 | MS-1 | $10^{-2}$ | 45 | 0.14 | 1.60 | 2.8 | >1.4* |
| 4 | S-2 | $10^{-3}$ | 30 | 0.16 | 1.50 | 2.2 | 0.60 |
| 5 | S-2 | $10^{-2}$ | 60 | 0.08 | 1.30 | 2.1 | 0.80 |
| 6 | MS-2/3 | $10^{-3}$ | 30 | 0.18 | 1.65 | 2.6 | 0.90 |
| 7 | MS-2/3 | $10^{-2}$ | 45 | 0.06 | 1.35 | 2.2 | >1.65* |

Notes:
[1] conc.: mole/mole AgNO$_3$
[2] S: relative sensitivity expressed as relative log Et values, lower figure means higher sensitivity;
[3] Delta Rereversal = overexposure latitude measured between dir. pos. density 0.1 + Dmin and rereversal density 0.1 + Dmin;
*rereversal density is still below 0.1 + Dmin at highest exposure level.

Table 2 illustrates the better direct positive sensitometry and the more extented overexposure latitude before encoutering rereversal when using the masked stabilizers in comparison to the free stabilizers. The results are most convincing with the mixture of compounds MS-2 and MS-3.

Example 2

A cubical silver bromide core-shell emulsion showing a final average grain size of 0.3 micron was prepared by simultaneous addition of equimolar solutions of silver nitrate and potassium bromide to a stirred aqueous gelatin solution. The precipitation of the core was carried out at 60° C. and at a pAg of 7.01. After addition of 50% of the total silver the core grains were chemically sensitized by means of $25.8 \times 10^{-3}$ mmole of sodium thiosulphate, $16.3 \times 10^{-3}$ mmole of aurochloric acid and $27.5 \times 10^{-3}$ mmole of p-toluenesulphonic acid sodium salt, all expressed per mole of silver halide. Then the grains were further grown under the same precipitation conditions until the final average grain size was reached. The gelatin/silver ratio was brought to 0.5 by the addition of extra gelatin and the core-shell emulsion was surface sensitized by means of $1.62 \times 10^{-3}$ mmole of p-toluenesulphonic acid sodium salt, $13.8 \times 10^{-3}$ mmole of sodium thiosulphate, $2.48 \times 10^{-3}$ of aurochloric acid and $26.8 \times 10^{-3}$ of ammoniumthiocyanate, all expressed per mole of silver halide.

The finished emulsion was divided in aliquot samples and to each sample were added 2.0 mmole/mole of $AgNO_3$ of spectral sensitizing dye SD-1 and 6.6 mmole/mole of $AgNO_3$ of nucleating agent phenylformylhydrazide. Finally various amounts of free 5-methylbenzotriazole (S-2) or masked methylbenzotriazole (a mixture of MS-2 and MS-3) were added as indicated in Table 3. Each emulsion sample was coated on a transparent support at a coverage of 4.0 Ag/m² expressed as $AgNO_3$. Then the coatings were exposed, developed during different times, fixed, washed, dried and evaluated as in example 1. The results are summarized in Table 3:

emulsion layers further contains a compound corresponding to general formula (I):

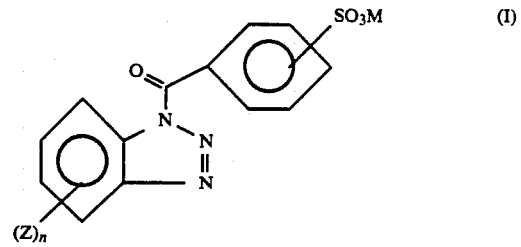

wherein Z represents a lower alkyl group, a nitro group or a halogen atom, n=0 to 4, and M represents a positive counterion.

2. Photographic direct positive material according to claim 1 wherein said material further contains a nucleating agent.

3. Photographic direct positive material according to claim 2 wherein said nucleating agent is an aryl hydrazide derivative.

4. Photographic direct positive material according to

TABLE 3a

| coating No | Stabi. | Conc.¹ | Dev · t · (s) | Sensitometry ||||
|---|---|---|---|---|---|---|---|
| | | | | Dmin | S² | Dmax | Delta RR³ |
| 8  | S-2    | $6 \times 10^{-3}$ | 35 | 0.04 | 1.35 | 1.39 | 1.35 |
| 9  | "      | "                  | 45 | 0.08 | 1.50 | 1.93 | 0.90 |
| 10 | "      | "                  | 60 | 0.15 | 1.65 | 2.77 | 0.60 |
| 11 | "      | $10^{-2}$          | 35 | 0.03 | 1.30 | 1.16 | 1.25 |
| 12 | "      | "                  | 45 | 0.05 | 1.35 | 1.32 | 1.05 |
| 13 | "      | "                  | 60 | 0.11 | 1.45 | 2.06 | 0.90 |
| 14 | MS-2/3 | $6 \times 10^{-3}$ | 35 | 0.05 | 1.50 | 2.22 | >1.50* |
| 15 | "      | "                  | 45 | 0.08 | 1.55 | 2.48 | 1.45 |
| 16 | "      | "                  | 60 | 0.14 | 1.60 | 3.27 | 0.60 |
| 17 | "      | $10^{-2}$          | 35 | 0.04 | 1.50 | 1.95 | >1.50* |
| 18 | "      | "                  | 45 | 0.05 | 1.50 | 2.37 | >1.50* |
| 19 | "      | "                  | 60 | 0.07 | 1.50 | 2.80 | >1.50* |

TABLE 3b

| coating No | Stabi. | Conc.¹ | Dev · t · (s) | Sensitometry 3 d 57°/34RH ||||
|---|---|---|---|---|---|---|---|
| | | | | Dmin | S² | Dmax | Delta RR³ |
| 8  | S-2    | $6 \times 10^{-3}$ | 35 | 0.06 | 1.50 | 1.78 | 1.25 |
| 9  | "      | "                  | 45 | 0.11 | 1.65 | 2.77 | 0.60 |
| 10 | "      | "                  | 60 | 0.53 | 1.65 | 3.09 | 0.40 |
| 11 | "      | $10^{-2}$          | 35 | 0.04 | 1.35 | 1.40 | 1.25 |
| 12 | "      | "                  | 45 | 0.07 | 1.40 | 2.19 | 1.00 |
| 13 | "      | "                  | 60 | 0.16 | 1.20 | 2.22 | 0.90 |
| 14 | MS-2/3 | $6 \times 10^{-3}$ | 35 | 0.06 | 1.50 | 2.22 | >1.50* |
| 15 | "      | "                  | 45 | 0.09 | 1.60 | 2.85 | >1.40* |
| 16 | "      | "                  | 60 | 0.13 | 1.70 | 3.24 | >1.30* |
| 17 | "      | $10^{-2}$          | 35 | 0.04 | 1.40 | 1.50 | >1.60* |
| 18 | "      | "                  | 45 | 0.05 | 1.50 | 1.92 | >1.50* |
| 19 | "      | "                  | 60 | 0.07 | 1.60 | 2.74 | >1.40* |

Notes:
1, 2, 3: cfr example 1.

The results of Table 3 again illustrate the better direct positive sensitometry and the more extended overexposure latitude before encoutering rereversal when using the masked methylbenzotriazoles in comparison to the free 5-methylbenzotriazole. Also the rereversal is better impeded after simulation of aging.

We claim:

1. Photographic direct positive material comprising a support and one or more radiation sensitive emulsion layers containing internal latent image-forming silver halide grains characterized in that at least one of said claim 2 wherein said nucleating agent is a N-substituted cycloammonium quaternary salt.

5. Photographic direct positive material according to claim 1 wherein said internal latent image forming silver halide grains are core-shell grains.

6. Photographic direct positive material according to claim 5 wherein the core of said core-shell grains is chemically ripened.

7. Photographic direct positive material according to any of claims 1 to 6 wherein said internal latent image-forming silver halide grains are internally doped with a polyvalent metal dopant.

8. Photographic direct positive material according to claim 7 wherein said polyvalent metal dopant is chosen from group VIII of the Periodic Table.

9. Photographic direct positive material according to claim 1 wherein said compound according to general formula (I) is present in a concentration comprised between $10^{-4}$ and $5 \times 10^{-2}$ mole per mole silver halide.

10. Photographic direct positive material according to claim 1 wherein said compound according to general formula (1) is 1-(2-sulphonatobenzoyl)-5-methyl-benzotriazole or 1-(2-sulphonatobenzoyl)-6-methyl-benzotriazole or a mixture of both.

11. Photographic direct positive material according to claim 1 which contains no intermediate non-light sensitive layer between the support and the emulsion layer(s).

12. A method for forming an image comprising imagewise exposing a photographic direct positive material according to claim 1, and developing said material (a) in the presence of a nucleating agent, or (b) with light flashing of said material during processing.

* * * * *